United States Patent
Kelland et al.

(10) Patent No.: US 10,722,699 B2
(45) Date of Patent: Jul. 28, 2020

(54) PLUG FOR OSMOMETRY SAMPLE CUP

(71) Applicant: Advanced Instruments, LLC, Norwood, MA (US)

(72) Inventors: James Kelland, E. Walpole, MA (US); Kevin J. Sullivan, Chestnut Hill, MA (US)

(73) Assignee: ADVANCED INSTRUMENTS, LLC, Norwood, MA (US)

( * ) Notice: Subject to any disclaimer, the term of this patent is extended or adjusted under 35 U.S.C. 154(b) by 49 days.

(21) Appl. No.: 16/306,618

(22) PCT Filed: Jun. 2, 2017

(86) PCT No.: PCT/US2017/035604
§ 371 (c)(1),
(2) Date: Dec. 3, 2018

(87) PCT Pub. No.: WO2017/210515
PCT Pub. Date: Dec. 7, 2017

(65) Prior Publication Data
US 2019/0336746 A1    Nov. 7, 2019

Related U.S. Application Data

(60) Provisional application No. 62/345,106, filed on Jun. 3, 2016.

(51) Int. Cl.
G01N 13/04    (2006.01)
A61M 39/20   (2006.01)
G01N 25/06   (2006.01)

(52) U.S. Cl.
CPC ............. *A61M 39/20* (2013.01); *G01N 13/04* (2013.01); *G01N 25/06* (2013.01)

(58) Field of Classification Search
CPC ............................. G01N 13/04; A61M 39/20
See application file for complete search history.

(56) References Cited

U.S. PATENT DOCUMENTS

| | | | |
|---|---|---|---|
| 3,063,288 A | 11/1962 | Reiff | |
| 3,164,982 A | 1/1965 | Pasternak et al. | |
| 3,248,932 A * | 5/1966 | Bohrer | G01N 13/04 73/64.47 |
| 3,263,487 A | 8/1966 | Fiske, Jr. | |
| 3,871,990 A * | 3/1975 | Hadermann | G01N 13/04 204/628 |
| 4,083,638 A | 4/1978 | Sandrock et al. | |
| 4,245,495 A | 1/1981 | Kakiuchi et al. | |
| 4,403,984 A * | 9/1983 | Ash | A61B 5/14528 600/364 |

(Continued)

FOREIGN PATENT DOCUMENTS

WO    2014164478 A1    10/2014

OTHER PUBLICATIONS

Extended European Search Report issued by the European Patent Office in corresponding European Patent Application No. 17807541.2, dated Dec. 17, 2019.

*Primary Examiner* — Gail Kaplan Verbitsky
(74) *Attorney, Agent, or Firm* — Arent Fox, LLP

(57) ABSTRACT

A plug for an osmometry sample cup or vial is provided that seals the sample cup or vial to prevent significant evaporation of a sample solution in the cup or vial prior to obtaining an osmolality measurement.

19 Claims, 7 Drawing Sheets

(56) References Cited

U.S. PATENT DOCUMENTS

| | | | |
|---|---|---|---|
| 4,657,409 A | | 4/1987 | Wiggin et al. |
| 4,784,811 A | * | 11/1988 | Hirschfeld ......... A61B 5/02154 |
| | | | 264/1.27 |
| 4,996,993 A | * | 3/1991 | York ...................... A61B 3/101 |
| | | | 324/692 |
| 5,279,793 A | * | 1/1994 | Glass ...................... G01N 13/04 |
| | | | 250/227.14 |
| 5,331,958 A | * | 7/1994 | Oppenheimer .... A61B 5/14535 |
| | | | 356/39 |
| 5,651,940 A | | 7/1997 | Buonaiuto et al. |
| 5,680,858 A | | 10/1997 | Hansen et al. |
| 5,753,186 A | | 5/1998 | Hanley et al. |
| 5,955,161 A | | 9/1999 | Tropsha |
| 6,234,004 B1 | | 5/2001 | Revsbech et al. |
| 6,921,395 B2 | | 7/2005 | Carano et al. |
| 7,182,509 B2 | | 2/2007 | Corbett |
| 8,460,620 B2 | | 6/2013 | Bartfeld et al. |
| 9,067,014 B2 | | 6/2015 | Nelson et al. |
| 9,162,228 B2 | | 10/2015 | Knight |
| 2014/0053988 A1 | | 2/2014 | Yamazaki |
| 2015/0037833 A1 | | 2/2015 | Fisher et al. |

\* cited by examiner

SECTION A-A

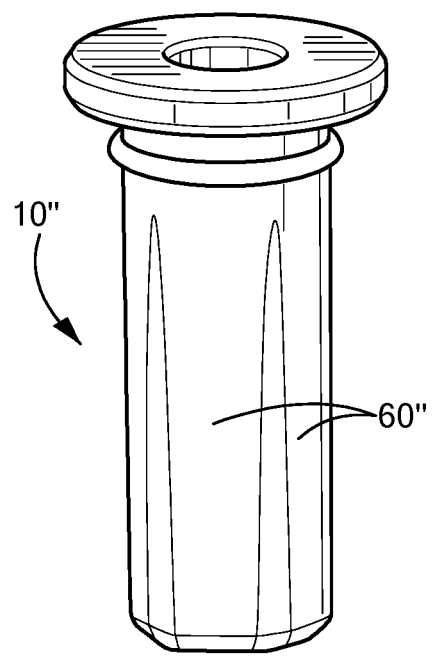
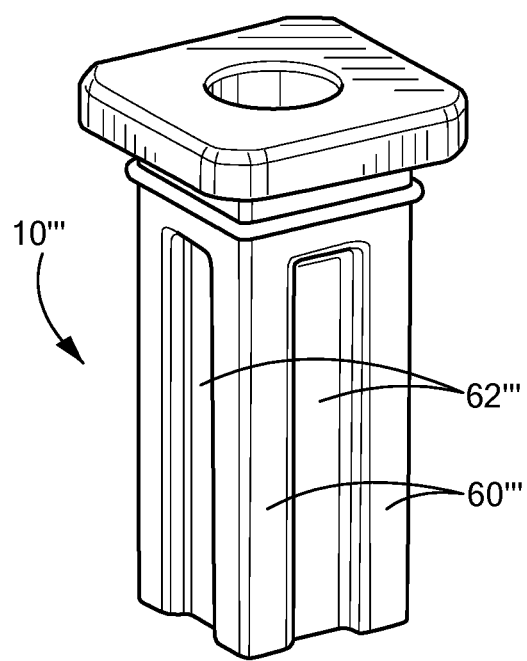
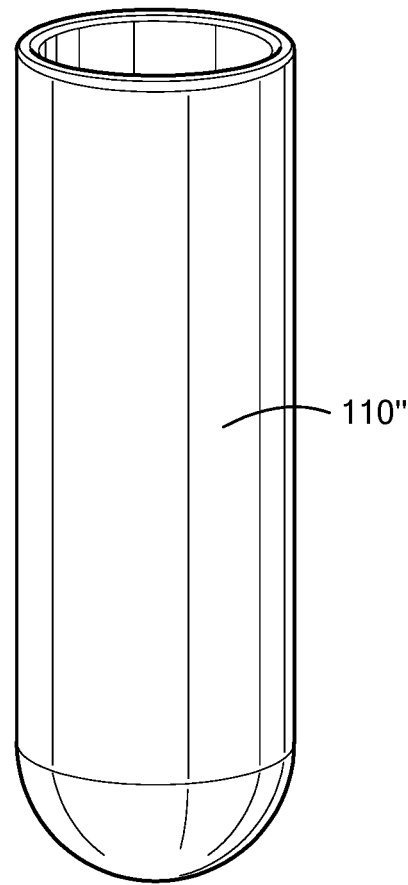
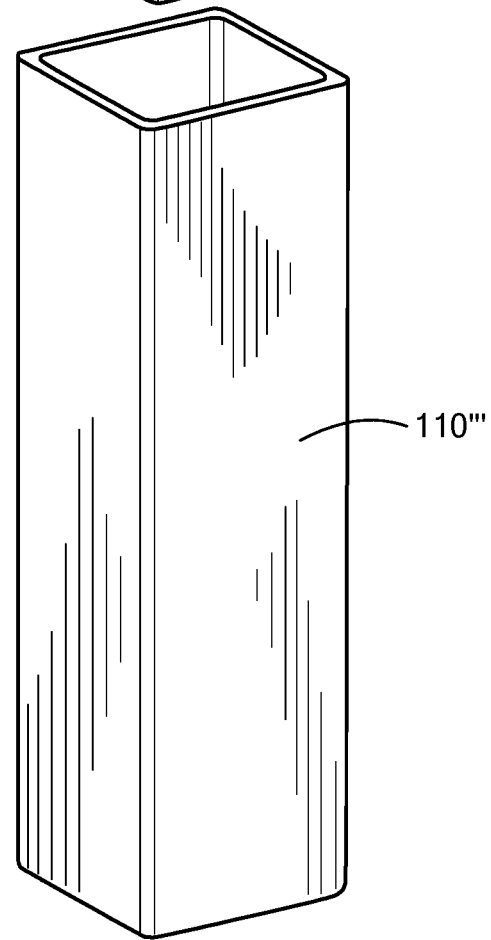
*FIG. 9*    *FIG. 10*

PLUG FOR OSMOMETRY SAMPLE CUP

CROSS REFERENCE TO RELATED APPLICATIONS

N/A

STATEMENT REGARDING FEDERALLY SPONSORED RESEARCH OR DEVELOPMENT

N/A

BACKGROUND

Osmolality is a measurement of the concentration of solute particles in a solvent. Osmometry measurements by the method of freezing point depression are conducted by supercooling a quantity of sample solution in a container, freezing the solution, and measuring its equilibrium melting temperature via a temperature probe that is inserted into the sample solution. The equilibrium melting temperature is representative of the concentration. The integrity of the sample concentration, cleanliness of the probe and, position of the probe within the sample volume are critical to obtaining accurate measurements.

There are many different size and style sample containers available for these measurements. Most containers are small (up to 1 mL), open-top plastic cups. Closed sample cups are available, but for these, the top must be opened or removed prior to running the test. For the occasional measurement of osmometry samples, these formats work quite well. However, many laboratories process several samples at about the same time and different instruments exist on the market that allow for the staging of multiple samples. For these workflow formats, the open and conventional closed-top sample cups are problematic.

The open cup allows sample solvent to evaporate from cups that have been filled but are waiting to be tested. Evaporation of the solvent concentrates the sample solution, yielding an artificially high test result. The open cup also has the potential for allowing dust and other airborne particles to contaminate the sample. Further, open sample cups may pose a biological hazard in the event that they are spilled.

The closed-top cups address the evaporation and contamination issues, but they introduce another complication in that they require operator intervention to open the cup immediately before testing. This intervention largely eliminates the possibility of staging multiple samples in advance.

Another important aspect to osmometry measurements is cleaning of the probe between samples. If the probe is not adequately cleaned, sample residue from one test can contaminate subsequent samples (commonly known as "carryover"). The predominant cleaning method currently used is to manually wipe the sensor probe with an absorbent wipe or pad of some sort. This separate step adds complication to the instrument and for the user, and increases overall test time. It is also imperfect in that the operator can forget to do the cleaning entirely. Also, operators often use slightly different techniques to clean, resulting in operator to operator variability. Automated systems often rely on a separate cleaning fluid flush or similar approach, again adding complexity and time to the overall process and instrument.

SUMMARY OF THE INVENTION

A plug for an osmometry sample cup or vial is provided that can address one or more of the issues of evaporation, cleaning, and temperature probe positioning for osmometry samples. The plug fits within an osmometry sample cup or vial to prevent significant evaporation of a sample solution in the cup or vial before an osmolality measurement can be made. The plug also helps to position a temperature probe properly within the sample cup or vial and helps to clean the temperature probe as it is inserted into and withdrawn from the cup or vial.

DESCRIPTION OF THE DRAWINGS

The invention will be more fully understood from the following detailed description taken in conjunction with the accompanying drawings in which:

FIG. 9 is an exploded view of a further embodiment of a plug with a sample vial;

FIG. 10 is an exploded view of a further embodiment of a plug with a sample vial having a square configuration;

DETAILED DESCRIPTION OF THE INVENTION

Figure 1:
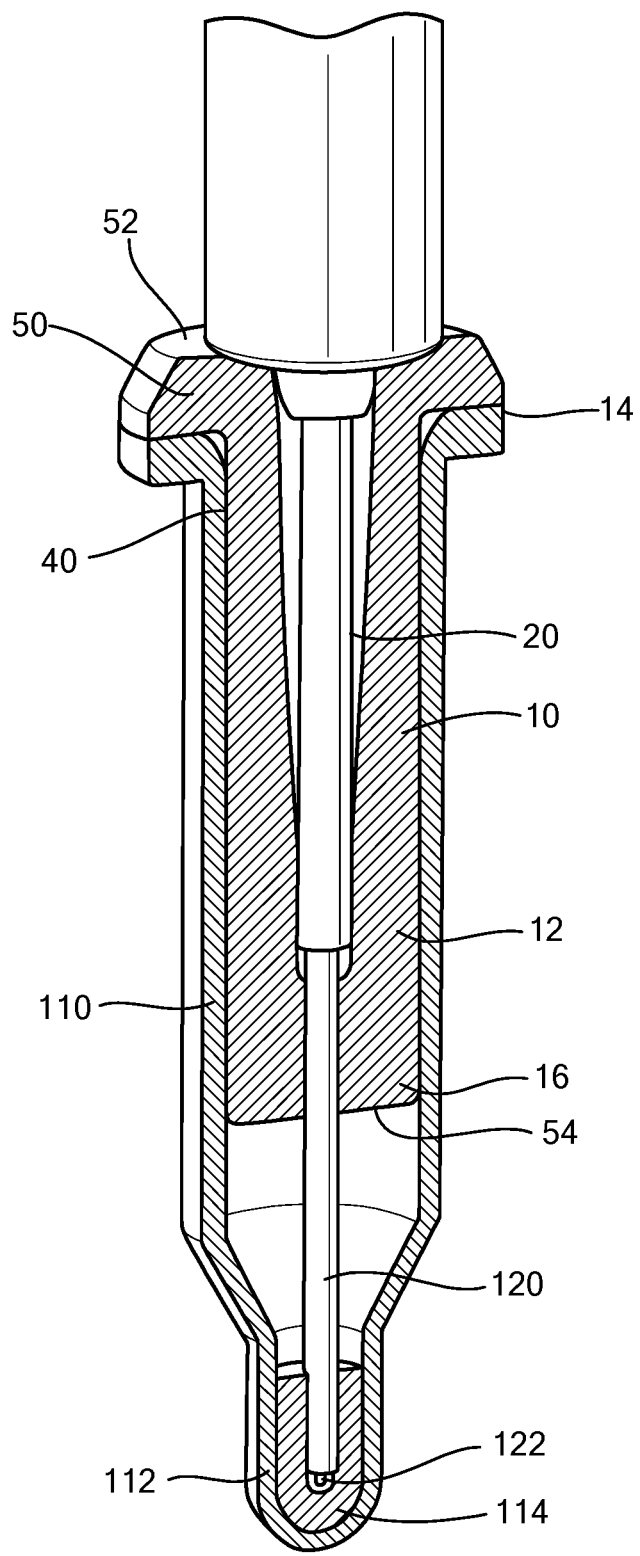
FIG. 1 is a cross-sectional view of an embodiment of a cylindrical sample cup plug assembled with an osmometry sample cup and temperature probe.
Figure 2:
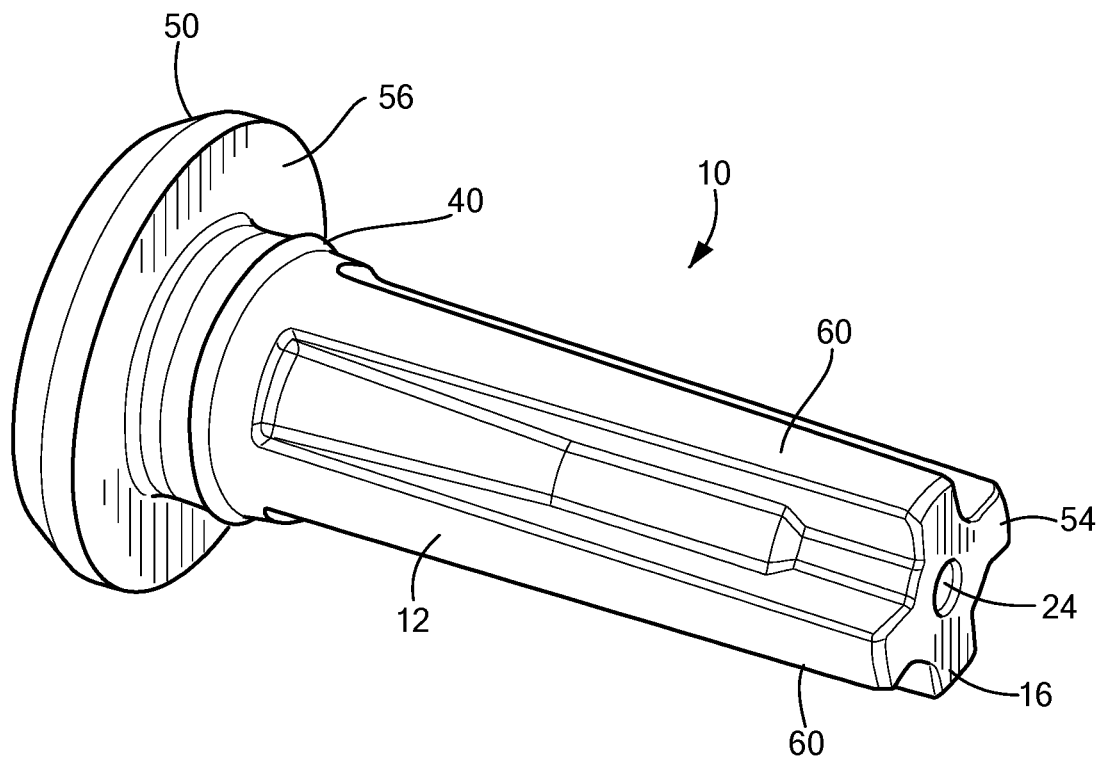
FIG. 2 is an isometric view of an embodiment of a cylindrical sample cup plug.
Figure 3:
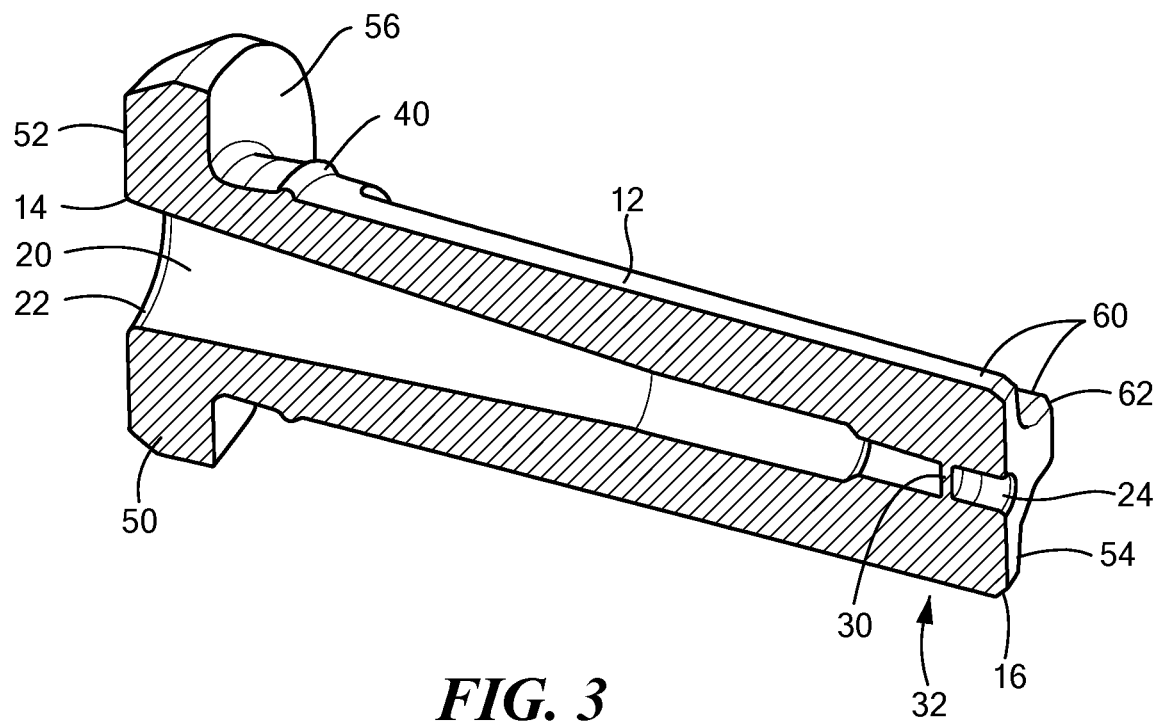
FIG. 3 is a cross-sectional view of the sample cup plug of FIG. 2.
Figure 4:
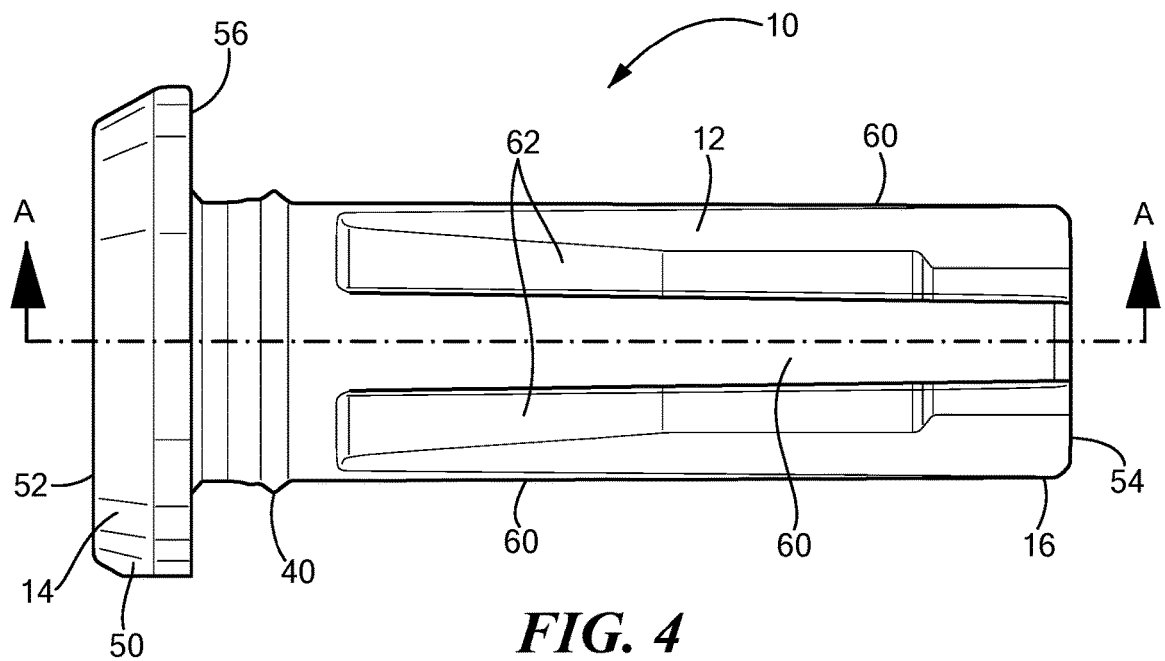
FIG. 4 is a side view of the sample cup plug of FIG. 2.
Figure 5:
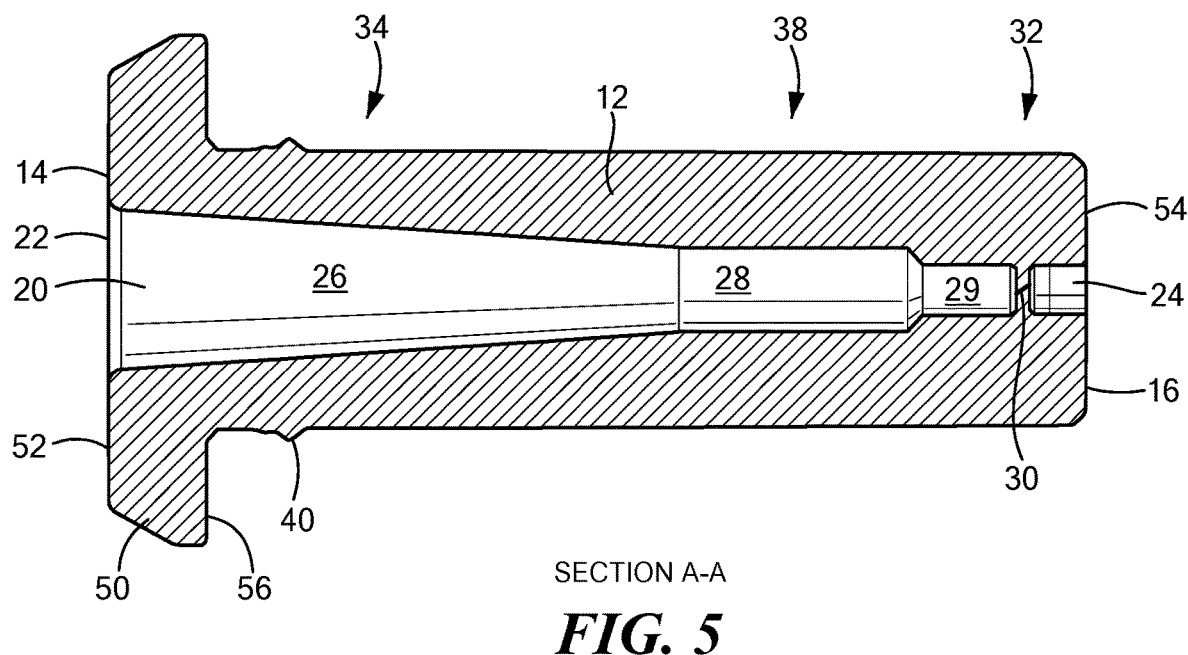
FIG. 5 is a cross-sectional view along line A-A of FIG. 4

One embodiment of a plug 10 for an osmometry sample cup 110 is illustrated in FIGS. 1-5. The plug 10 is inserted in a sample cup which contains, in a well 112 at the bottom of the cup, a solution 114 to be tested. A temperature probe 120 has been inserted through the plug into the sample in the well of the cup. The plug includes an internal passage 20 and flange 50, which aid in positioning the probe properly in the sample. The plug also includes a diaphragm 30, which can be penetrated by the probe during insertion, and one or more sealing elements 40 for sealing engagement with the cup. The diaphragm and sealing element(s) together provide a fluidic seal to prevent significant evaporation of a sample from the cup prior to insertion of the probe. The diaphragm also assists in cleaning the probe between samples.

In some embodiments, the plug 10 has a body 12 extending longitudinally from a proximal end 14 to a distal end 16. The internal passage 20 extends longitudinally through an interior of the body from an opening 22 at the proximal end 14 to an opening 24 at the distal end 16. The diaphragm 30 extends transversely across the passage 20 in a distal region 32 of the body. The temperature probe 120 can be inserted through the passage 20 in the plug 10, penetrating the diaphragm 30, into a volume of sample solution 114 in the well 112 at the bottom of the sample cup 10.

The well 112 of the sample cup 110 is typically cylindrically shaped with a hemispherical bottom. The sample cup and well can be sized to hold any desired sample volume.

Figure 12:
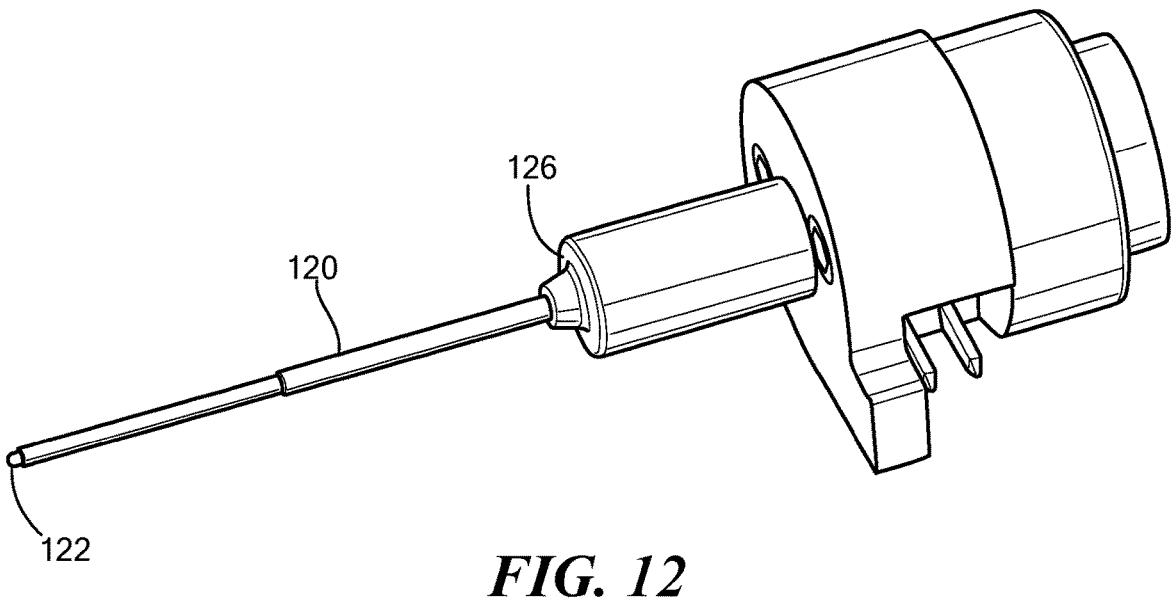
FIG. 12 is an isometric view of a temperature probe for use with the sample cup and sample cup plug.

Sample volumes for osmometry typically range from 10 μL to 10 mL. The thermistor tip 122 of the probe 120 is preferably placed within the volume of sample solution at the center of the hemisphere, radially equidistant from the interior walls of the well 112. A typical temperature probe is illustrated in FIG. 12. The temperature probe can be lowered into, and raised out of, the sample cup by, for example, a stepper motor and lead screw or similar electro-mechanical positioning system. Often, the systems that lower and raise the probe have significant positional variability so that it is difficult to accurately and repeatedly locate the probe within the sample volume. The plug reduces this variability by providing a locating face 52 at the proximal end which provides a physical stop for an accompanying face 126 on the temperature probe. The plug 10 also serves to center the probe 120 within the cup 110 so that the tip 122 can be placed at the optimal location centered in the well.

In some embodiments, the internal passage 20 of the plug 10 has a conically shaped lead-in opening portion 26 at a proximal region 34 to guide the temperature probe to the radial center of the body. The passage 20 is wider in diameter at the proximal end 14 and gradually tapers toward the distal end 16. The passage can have a cylindrical portion 28 at a middle region 38 of the body. The passage can further include a more narrow cylindrical portion 29. The diameter of the most narrow cylindrical portion can generally conform to the outer diameter of the probe at and near the tip 122. The narrow cylindrical portion or portions help to retain the probe in a radially centered position. When the plug is fully inserted in the sample cup, the underside face 56 of the proximal flange 50 is in contact with the top of the sample cup, and a distal face 54 of the plug is preferably located sufficiently above the surface of the sample solution such that any splash from the sample solution does not reach and adhere to the distal face of the plug.

Figure 6C:
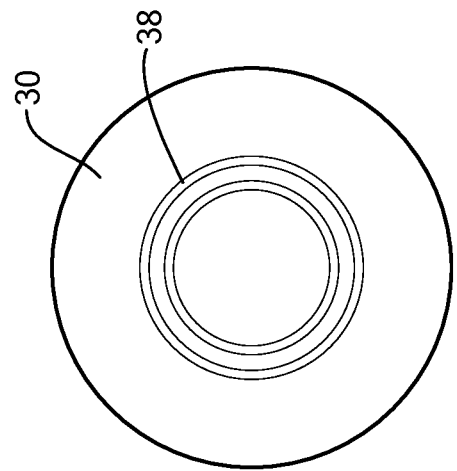
FIGS. 6A-6C are illustrations of diaphragms with weakened sections.
Figure 6B:
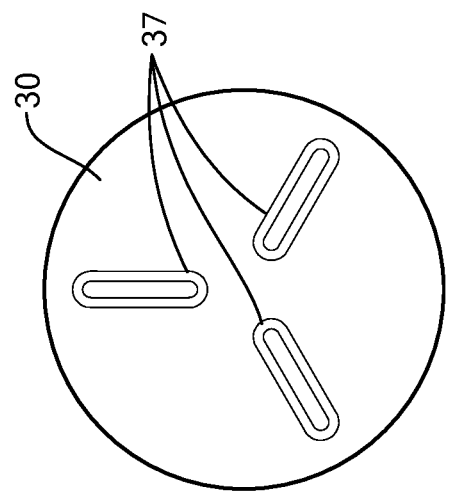
Figure 6A:
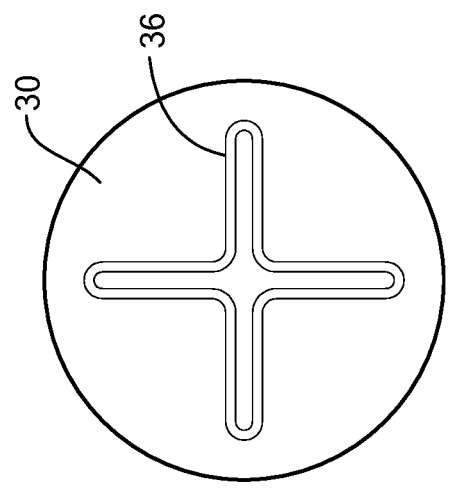

The penetrable diaphragm 30 is located within the passage 20 in the distal region 32 of the plug, close to the distal end 16 of the passage. The diaphragm helps to prevent significant evaporation of the sample solution in the cup before an osmolality measurement can be made. The diaphragm thickness and material is such that it is easily penetrable by the probe. In some embodiments, the thickness of the diaphragm can range from 0.005 to 0.025 inch. In some embodiments, the diaphragm has a durometer hardness ranging from 60 to 80 Shore A. In some embodiments, the diaphragm can extend continuously across the passage until pierced by the probe. In some embodiments, the diaphragm can have a localized weak area, such as one or more slits or small holes or a thinner area or areas, that is easily penetrable while still achieving a high degree of fluid sealing. A thinner weak area can be thinned down either during a molding process or post-mold via hot pressing, stamping, or the like. FIGS. 6A-6C illustrate three patterns for a thinner area of a diaphragm 30. FIG. 6A illustrates a thinned area 36 in the shape of a cross or X. FIG. 6B illustrates thinned areas 37 as three radial lines. FIG. 6C illustrates a thinned area 38 in the shape of a circle or ring. Being thinner than the surrounding diaphragm material, the thinner area tears more readily, making it easier for a probe to penetrate the diaphragm.

The diaphragm 30 also serves to wipe the length of the temperature probe 120 as the probe is inserted into and withdrawn from the sample cup 110. The ability to wipe the probe as it is withdrawn from the sample cup is advantageous, because it ensures that any residual thin fluid film does not have time to dry on the probe. In prior art osmometer systems, the probe is withdrawn and then wiped or cleaned some moments later. The interval between the withdrawal and the cleaning of the probe can be long enough to allow the thin fluid film to dry. The dry film can be more difficult to remove and may gradually build up in thickness over time. This can result in contamination of subsequent samples—commonly referred to as "carry-over."

A sealing element 40 is located circumferentially around the perimeter of the body 12 for sealing engagement with the inner wall of the sample cup. The sealing element 40 and the diaphragm 30 together provide a fluidic seal of the sample cup. In this manner, fluid in the sample cup cannot evaporate out of the cup in an amount sufficient to adversely affect the osmolality measurement of the sample solution.

In the embodiment shown in FIGS. 1-5, the sealing element 40 is half circular in cross-section. In other embodiments, the sealing element can take other forms, such as square, rectangular, and the like. In addition to fluid sealing, the sealing element can also provide a frictional force against the sample cup that prevents the plug from falling out in the event that the sample cup is dropped or mishandled by the user. The sealing element can be formed integrally with the body or can be provided as a separate piece, such as an O-ring placed in an exterior circumferential groove in the body. Multiple sealing elements can be incorporated depending on the particular requirements of the application. For example, two sealing elements can be used with larger sample cups.

In some embodiments, a flange 50 can be located at the proximal end 14 of the plug. The flange provides a surface 56 that can engage with the top edge of the sample cup 110. The flange can also provide a mechanism for positioning the temperature probe 120 axially within the cup by providing a surface 52 for supporting a complementary surface 126 of the temperature probe. In embodiments where the flange is omitted, axial locating of the plug within the cup may be achieved by other features.

The outer surface of the body 12 of the plug can include a number of ribs 60 that extend axially along a portion of the length of the body. The outer diameter of the ribs can be selected to contact the inner surface of the sample cup in which the plug is intended to be used. The ribs locate the plug centrally within the sample cup. Any desired number of ribs can be used. Four ribs are shown in the embodiment of FIGS. 1-5. Channels 62 between the ribs can serve as vent passages for air as the plug is being inserted into the sample cup. The sealing member 40 can provide a tactile signal, such as by "clicking" into place at the top of the sample cup 110, to indicate that the plug is fully seated within the sample cup and the sample is sealed therein.

Figure 7:
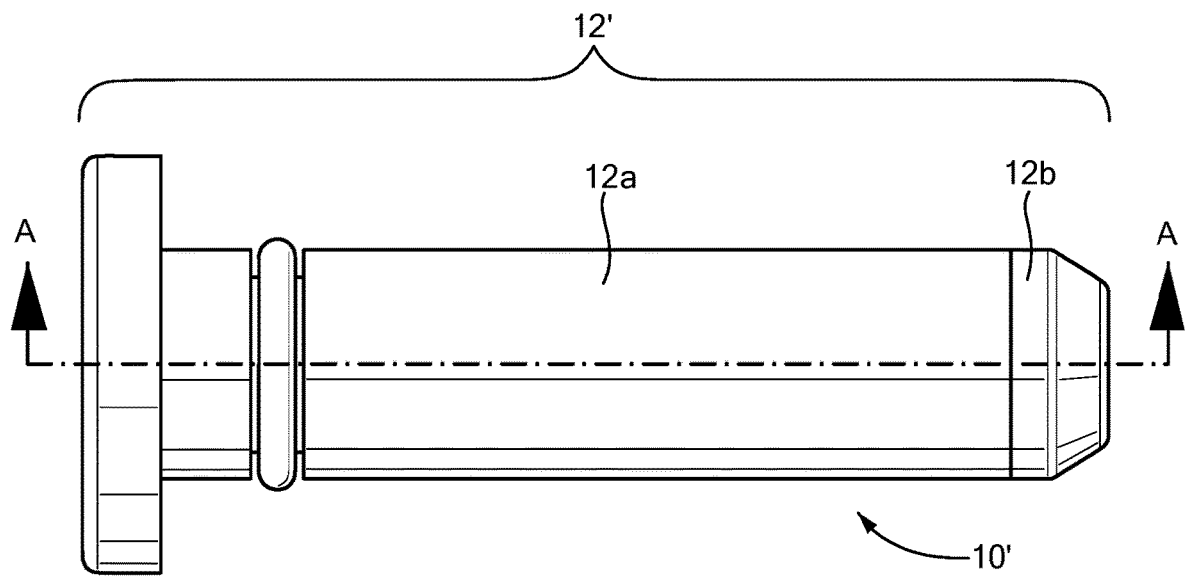
FIG. 7 is a side view of a plug formed from multiple components.
Figure 8:
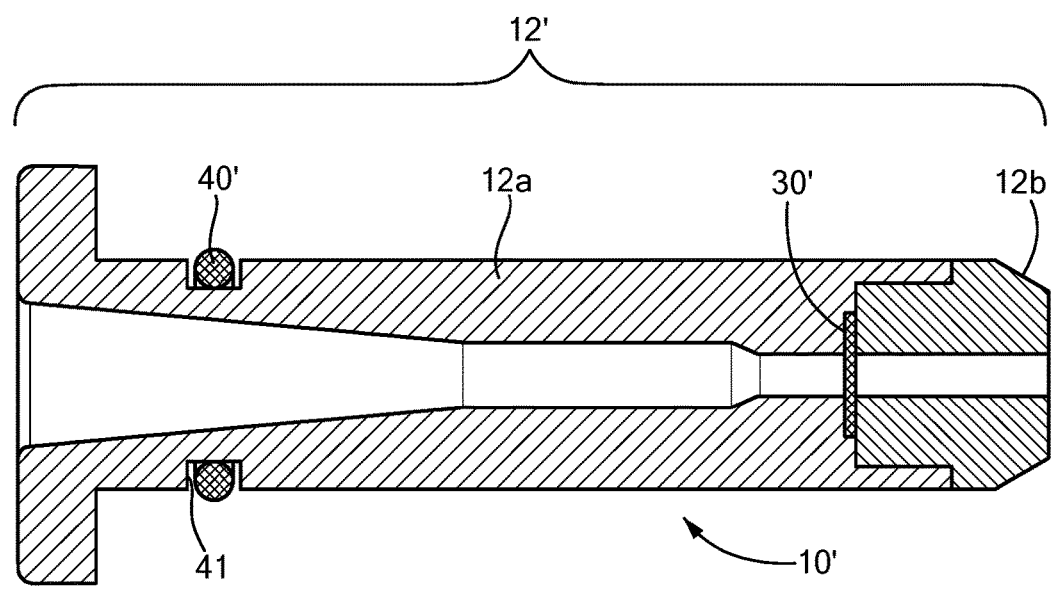
FIG. 8 is a cross-sectional view of the plug of FIG. 7.

FIGS. 7 and 8 illustrate an embodiment of a plug 10' formed from multiple separate pieces assembled together. The plug body 12' includes a proximal body component 12a and a distal body component 12b. The diaphragm 30' is formed separately and is held in place between the proximal and distal body components. The sealing element 40' is a separate O-ring and can be held in a circumferential groove 41 around the outside of the proximal body component 12a. The proximal and distal body components can be formed of a thermoplastic material, which can be molded or machined. The two body components can be attached in any suitable manner with the diaphragm in between. For example, the two components can be threaded, glued, ultrasonically welded, or press fit. The O-ring 40' can be formed of an elastomeric material and either placed over the proximal body component or overmolded directly onto the proximal body component (commonly called "two-shot" molding). The diaphragm 30' can be formed from an elastomeric, thermoplastic, or foil laminate material. In some embodiments, the diaphragm can be overmolded onto or adhered to either the proximal body component or the distal body component. In some embodiments, the diaphragm can be inserted between the proximal and distal body components and retained there once the proximal and distal body components are attached together.

FIG. 9 illustrates a further embodiment of a plug 10″ configured to fit in sealing engagement with a 2 mL glass or plastic sample vial 110″. The exterior surface of the plug can include a larger number of ribs 60″, such as 5 or 6 ribs, because the vial is larger than the sample cup illustrated in the embodiment of FIGS. 1-5. The interior of the plug can be substantially as shown in FIGS. 1-5.

FIG. 10 illustrates a still further embodiment of a plug 10‴ configured to fit in sealing engagement with a vial 110‴ having a square configuration. The exterior surface of the plug can include corners that serve as ribs 60′ and the exterior faces of the plug can have channels 62″ formed therein that serve as vent passages for air as the plug is being inserted into the vial. The interior of the plug can be substantially as shown in FIGS. 1-5.

It will be appreciated that sample cups and vials can be manufactured in many sizes and configurations, and the plug described herein can be similarly manufactured in any complementary size and configuration.

The plug can be made of any suitable material. The plug material can be elastomeric, thermoplastic, or a combination of these materials in order to achieve the desired sealing and sliding characteristics as it is inserted into the sample cup. In some embodiments, the plug can be made from a thermoplastic elastomer or silicone. In some embodiments, the plug body can be made from a harder material, such as a polyethylene, while the sealing element and diaphragm are made from other materials suitable for their purposes. In some embodiments, thinned areas can be incorporated into a diaphragm that is made from a thermoplastic elastomer, thermoplastic polymer, or foil laminate. In some embodiments, the diaphragm is made from an elastomeric material having a durometer hardness ranging from 40 to 80 Shore A. In some embodiments, the diaphragm is made from a thermoplastic material having a durometer hardness ranging from 45 to 75 Shore D.

The plug can be manufactured in any suitable manner. In some embodiments, the plug can be manufactured by machining, injection molding, overmolding, casting, or by one of several rapid manufacturing methods, such as stereolithography, fused deposition, or selective sintering.

In operation, to perform an osmolality measurement on a solution, a volume of a sample solution to be measured is placed in a sample cup. The sample cup is sealed by inserting a plug into the sample cup. The sealed sample cup is placed in an osmometer. Some osmometers include a carousel or rack in which a number of sample cups can be staged at one time.

At an appropriate time, the sealed sample cup is transferred to a cooling chamber, and a temperature probe is inserted through the passage in the plug, penetrating the diaphragm, until the tip reaches the appropriate location within the sample solution in the well of the cup. The osmometer then supercools the sample solution. When the temperature of the sample solution has decreased to a sufficiently low temperature, freezing of the solution is initiated. The freezing process may be initiated by any one of several methods, such as, without limitation, mechanical pulse, ultrasonic pulse, or cold wire. Immediately after freezing, cooling is discontinued, and the temperature of the sample solution within the sample cup then rises until it reaches a plateau, which is the equilibrium melting temperature of the solution. The equilibrium melting temperature is indicative of the osmolality, or concentration of the solute in solution in the solvent.

Figure 11:
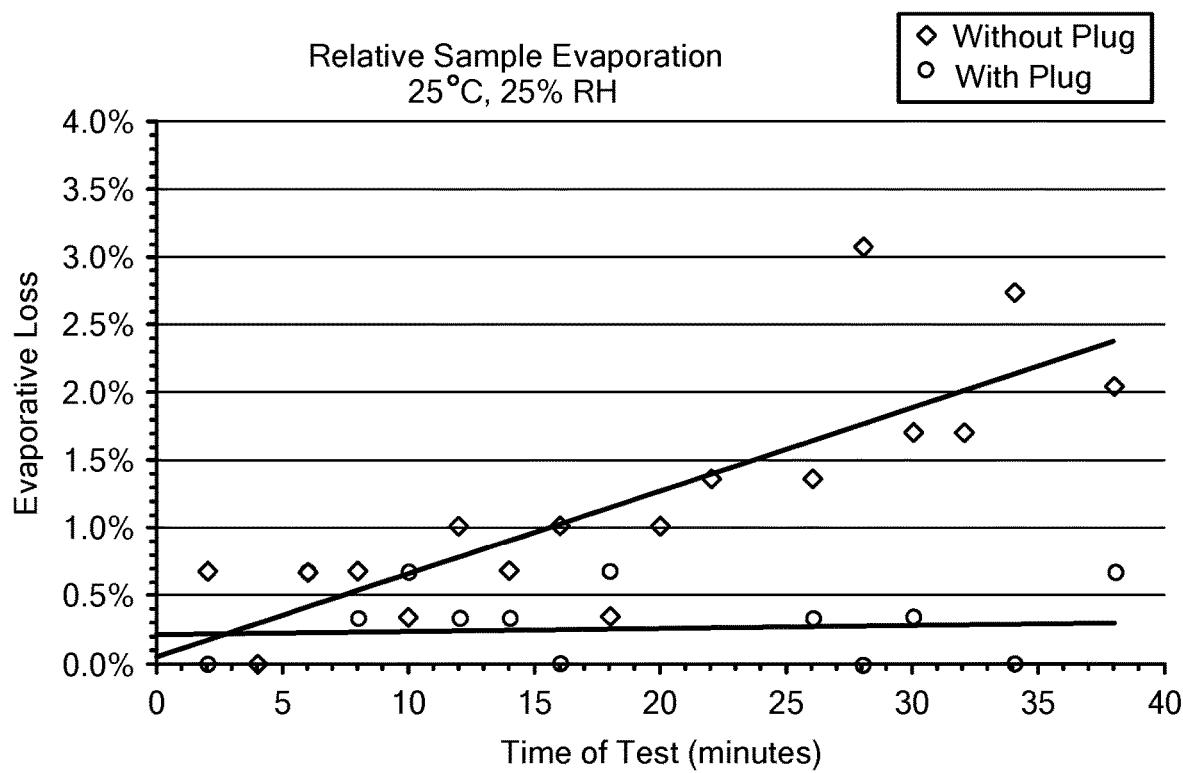
FIG. 11 is a graph illustrating sample evaporative loss over time with and without the plug.

FIG. 11 illustrates test data in which the evaporative loss from a number of sample cups was measured over time with and without a plug as described herein. The diamonds illustrate the evaporative loss from sample cups without a plug, and the circles illustrate the evaporative loss from sample cups with a plug. The horizontal axis indicates the length of time from when a sample volume was placed into a sample cup until the sample could be tested.

It can be seen that in samples without a plug, the volume of sample lost to evaporation increased linearly over time, indicated by an upwardly sloping line fit to the diamond data points. The volume of sample in the cups with a plug remained low and relatively constant, indicated by the substantially horizontal line fit to the circle data points.

Other aspects and embodiments of the plug for an osmometry sample cup include the following:

1. A plug for an osmometry sample cup or vial, comprising:
a body extending longitudinally from a proximal end to a distal end, a passage extending longitudinally through an interior of the body from an opening at the proximal end to an opening at the distal end;
a diaphragm extending transversely across the passage in a distal region of the body, the diaphragm formed of a material penetrable by a tip of an osmometer temperature probe.

2. The plug of embodiment 1, wherein the diaphragm has a thickness ranging from 0.005 to 0.025 inch.

3. The plug of any of embodiments 1-2, wherein the diaphragm comprises an elastomeric material having a durometer hardness ranging from 40 to 80 Shore A or a thermoplastic material having a durometer hardness ranging from 45 to 75 Shore D.

4. The plug of any of embodiments 1-3, wherein the diaphragm includes a weakened area.

5. The plug of embodiment 4, wherein the weakened area of the diaphragm comprises one or more slits or holes.

6. The plug of any of embodiments 1-5, further comprising a sealing element disposed circumferentially around an exterior surface of the longitudinal body at a proximal region of the longitudinal body.

7. The plug of any of embodiments 1-6, further comprising a plurality of sealing elements disposed circumferentially around an exterior surface of the longitudinal body at a proximal region of the longitudinal body.

8. The plug of any of embodiments 1-7, further comprising a plurality of guide ribs extending longitudinally along an exterior surface of the longitudinal body.

9. The plug of embodiment 8, wherein the ribs are spaced symmetrically about the exterior of the longitudinal body.

10. The plug of any of embodiments 1-9, further comprising a flange disposed about the proximal end of the body.

11. The plug of any of embodiments 1-10, wherein the passage through the longitudinal body is tapered from the distal opening to a mid-region of the longitudinal body.

12. The plug of any of embodiments 1-11, wherein the body is formed of a thermoplastic elastomeric material or a silicone material.

13. The plug of any of embodiments 1-12, wherein the plug is sized to accommodate an osmometer sample cup or vial having a sample volume ranging from 10 μL to 10 mL.

14. An osmometry sample cup assembly comprising:
an osmometry sample cup; and the plug of any of embodiments 1-13, wherein the plug is sized to fit within and seal the osmometer sample cup.

15. A method of performing an osmolality measurement on a sample solution, comprising:
placing a volume of the sample solution in a sample cup or vial;
sealing the sample cup or vial with the plug of any of embodiments 1-13;
penetrating the diaphragm in the plug with a temperature probe;
supercooling the sample;
initiating freezing of the sample; and
obtaining temperature measurements of the sample solution in the sample cup or vial.

16. The method of embodiment 15, further comprising:
penetrating the seal in the plug with the temperature probe after a time of greater than 1 minute.

17. The method of any of embodiments 15-16, further comprising:
wiping the temperature probe clean as it is pulled out of the plug.

18. The method of any of embodiments 15-17, wherein the sample solution is selected from the group consisting of blood, serum, plasma, urine, milk, and cell culture media.

19. The method of any of embodiments 15-18, wherein the sample solution is an aqueous based solution.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A plug for an osmometry sample cup or vial, comprising:
a body extending longitudinally from a proximal end to a distal end, a passage extending longitudinally through an interior of the body from an opening at the proximal end to an opening at the distal end;
a diaphragm extending transversely across the passage in a distal region of the body, the diaphragm formed of a material penetrable by a tip of an osmometer temperature probe.

2. The plug of claim 1, wherein the diaphragm has a thickness ranging from 0.005 to 0.025 inch.

3. The plug of claim 1, wherein the diaphragm comprises an elastomeric material having a durometer hardness ranging from 40 to 80 Shore A or a thermoplastic material having a durometer hardness ranging from 45 to 75 Shore D.

4. The plug of claim 1, wherein the diaphragm includes a weakened area.

5. The plug of claim 4, wherein the weakened area of the diaphragm comprises one or more slits or holes.

6. The plug of claim 1, further comprising a sealing element disposed circumferentially around an exterior surface of the longitudinal body at a proximal region of the longitudinal body.

7. The plug of claim 1, further comprising a plurality of sealing elements disposed circumferentially around an exterior surface of the longitudinal body at a proximal region of the longitudinal body.

8. The plug of claim 1, further comprising a plurality of guide ribs extending longitudinally along an exterior surface of the longitudinal body.

9. The plug of claim 8, wherein the ribs are spaced symmetrically about the exterior of the longitudinal body.

10. The plug of claim 1, further comprising a flange disposed about the proximal end of the body.

11. The plug of claim 1, wherein the passage through the longitudinal body is tapered from the distal proximal opening to a mid-region of the longitudinal body.

12. The plug of claim 1, wherein the body is formed of a thermoplastic elastomeric material or a silicone material.

13. The plug of claim 1, wherein the plug is sized to accommodate an osmometer sample cup or vial having a sample volume ranging from 10 µL to 10 mL.

14. An osmometry sample cup assembly comprising:
an osmometry sample cup; and
the plug of claim 1, wherein the plug is sized to fit within and seal the osmometer sample cup.

15. A method of performing an osmolality measurement on a sample solution, comprising:
placing a volume of the sample solution in a sample cup or vial;
sealing the sample cup or vial with the plug of claim 1;
penetrating the diaphragm in the plug with a temperature probe;
supercooling the sample;
initiating freezing of the sample; and
obtaining temperature measurements of the sample solution in the sample cup or vial.

16. The method of claim 15, further comprising:
penetrating the diaphragm in the plug with the temperature probe after a time of greater than 1 minute.

17. The method of claim 15, further comprising:
wiping the temperature probe clean as it is pulled out of the plug.

18. The method of claim 15, wherein the sample solution is selected from the group consisting of blood, serum, plasma, urine, milk, and cell culture media.

19. The method of claim 15, wherein the sample solution is an aqueous based solution.

* * * * *